United States Patent [19]

Domagala et al.

[11] Patent Number: 4,578,473

[45] Date of Patent: Mar. 25, 1986

[54] PROCESS FOR QUINOLINE-3-CARBOXYLIC ACID ANTIBACTERIAL AGENTS

[75] Inventors: John M. Domagala, Canton; Mel C. Schroeder, Ann Arbor, both of Mich.

[73] Assignee: Warner-Lambert Company, Morris Plains, N.J.

[21] Appl. No.: 723,019

[22] Filed: Apr. 15, 1985

[51] Int. Cl.[4] ............................................ C07D 215/22
[52] U.S. Cl. ..................... 546/156; 546/14; 544/128; 544/363; 548/409
[58] Field of Search .................. 546/156, 14; 544/128, 544/363

[56] References Cited

FOREIGN PATENT DOCUMENTS 3318145 11/1984 Fed. Rep. of Germany ...... 546/157

Primary Examiner—Donald G. Daus
Assistant Examiner—Robert Benson
Attorney, Agent, or Firm—Ronald A. Daignault

[57] ABSTRACT

An improved process for the preparation of 7-substituted amino-1-cyclopropyl-6,8-difluoro-1,4-dihydro-4-oxo-3-quinolinecarboxylic acids is described where an alkyl ester of a 6,7,8-trifluoro precursor is converted to a trialkylsilyl ester which fluorine at $C_7$ is directly displaced to the desired product.

21 Claims, No Drawings

PROCESS FOR QUINOLINE-3-CARBOXYLIC ACID ANTIBACTERIAL AGENTS

BACKGROUND OF THE INVENTION

Belgium Pat. No. 899,399 describes certain 7-piperazine-1-cyclopropyl-6,8-difluoro-1,4-dihydro-4-oxo-3-quinolinecarboxylic acids. German Offenlegungschrift No. 3318145 describes various 7-amino-1-cyclopropyl-6,8-difluoro-1,4-dihydro-4-oxo-3-quinolinecarboxylic acids. European Patent Publication No. 106489 describes 7-cyclic amine-1-cyclopropyl-6,8-difluoro-1,4-dihydro-4-oxo-3-quinolinecarboxylic acids.

All of the above compounds are useful as antibacterial agents and have been described as being prepared by displacement of a 7-fluoro atom from a compound of the formula

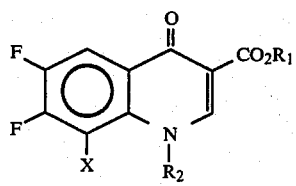

wherein X is hydrogen or fluorine; $R_1$ is hydrogen or lower alkyl, and $R_2$ is alkyl of one to three carbon atoms or cycloalkyl of three to six carbon atoms, with the appropriate amine.

The object of the present invention is an improved process for preparing the compounds described above by converting a lower alkyl ester of 1-alkyl or cycloalkyl-6,7,8-trifluoro or 6,7-difluoro-1,4-dihydro-4-oxo-3-quinolinecarboxylic acid to a silyl ester thereof which can be directly used in the displacement reaction with the amine displacing the 7-fluoro to give the final product. The present method provides better quality material with fewer purification procedures, step-saving by being able to carry out the reaction in one-pot, and practically quantitative yields from the 1-alkyl or 1-cycloalkyl-6,7,8-trifluoro or 6,7-difluoro-1,4-dihydro-4-oxo-3-quinolinecarboxylic acid alkyl esters.

SUMMARY OF THE INVENTION

Accordingly the present invention is related to an improved process for the preparation of a compound of the formula

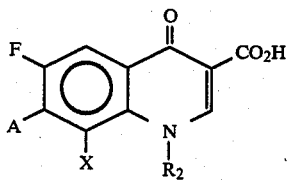

I and the pharmaceutically acceptable acid addition or base salts thereof, wherein A is a substituted amino group; X is hydrogen or fluorine, and $R_2$ is alkyl of one to three carbon atoms or cycloalkyl of three to six carbons, which comprises:

(a) reacting 1.0–3.0 equivalents of an iodotrialkylsilane in an inert solvent with a compound of the formula

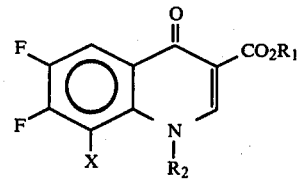

II wherein $R_2$ and X are as defined above and $R_1$ is alkyl of one to three carbon atoms, and heating the reaction mixture until the reaction is complete at 30°–100° C. to form a trialkylsilyl ester thereof;

(b) adding at least one equivalent of the appropriate amine to the trialkylsilyl ester in an aprotic solvent or an aprotic co-solvent and heating the reaction mixture between 60° and 120° C. until the reaction is complete; and if desired, converting by known means the resulting compound of formula I to a pharmaceutically acceptable acid addition or base salt thereof.

DETAILED DESCRIPTION

The term "alkyl" in the present invention generally refers to a one to three carbon straight or branched hydrocarbon radical, such as, e.g., ethyl, 1- or 2-propyl, and preferably methyl.

"Cycloalkyl" refers to a three to six-membered saturated hydrocarbon ring such as, e.g., cyclobutyl, cyclopentyl, cyclohexyl, and preferably, cyclopropyl.

By substituted amino group, there is included a mono- or dialkylamino group of one to four carbon atoms, straight or branched, which alkyl portion may be optionally substituted by hydroxy, amino, methylamino or dimethylamino; a five- to six-membered heterocyclic amino group, which ring may be interrupted by another heteroatom such as oxygen, sulfur, —SO—, —SO$_2$ or N—R$_3$, and which ring may be substituted by alkyl of one to three carbon atoms, hydroxy, alkoxy of one to three carbon atoms, amino, methylamino, ethylamino, aminomethyl, aminoethyl, alkylaminoethyl, or alkylaminomethyl, in which alkyl is one to three carbon atoms, and wherein R$_3$ is hydrogen, alkyl of one to four carbon atoms or cycloalkyl having three to six carbon atoms.

Also included as substituted amino is a group of the formula

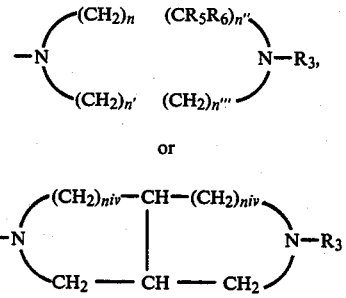

wherein $R_3$ is as defined above, and
n is 1, 2, 3, or 4;
n′ is 1, 2, 3, or 4 wherein n+n′ is a total of 2, 3, 4, or 5;
n″ is 0, 1, or 2;
n‴ is 1 to 5; and
n$^{iv}$ is 1 or 2.

Further there is included as substituted amino a bicyclic amino group, such as those selected from

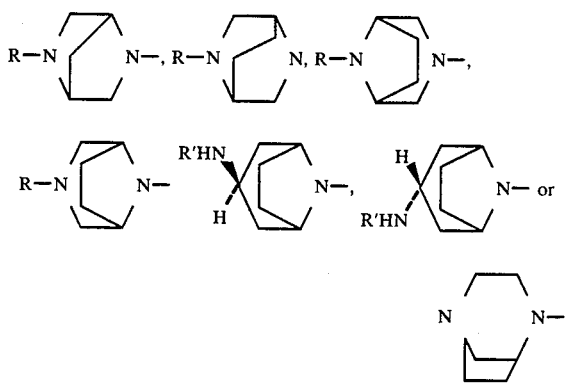

in which R is hydrogen, alkyl of one to three carbon atoms, hydroxyalkyl of two or three carbon atoms, benzyl or p-aminobenzyl, and R' is hydrogen or alkanoyl of one to three carbon atoms.

Preferred amino groups are piperazine or N-methylpiperazine; a pyrrolidine of the formula

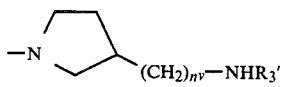

in which $n^v$ is 0 or 1 and $R_3'$ is hydrogen, methyl, ethyl, 1- or 2-propyl; a spiroamine of the formula

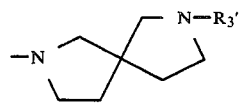

in which $R_3'$ is as defined above, or the above bridged amino groups in which R and R' are also defined above.

Particularly preferred 7-substituted amino-1-cyclopropyl-6,8-difluoro-1,4-dihydro-4-oxo-3-quinolinecarboxylic acids prepared by the improved process of the present invention are the following:

7-[3-(aminomethyl)-1-pyrrolidinyl]-1-cyclopropyl-6,8-difluoro-1,4-dihydro-4-oxo-3-quinolinecarboxylic acid;

1-cyclopropyl-7-[3-[(ethylamino)methyl]-1-pyrrolidinyl]-6,8-difluoro-1,4-dihydro-4-oxo-3-quinolinecarboxylic acid;

1-ethyl-7-[3-[(ethylamino)methyl]-1-pyrrolidinyl]-6,8-difluoro-1,4-dihydro-4-oxo-3-quinolinecarboxylic acid;

7-[3-amino-1-pyrrolidinyl]-1-cyclopropyl-6,8-difluoro-1,4-dihydro-4-oxo-3-quinolinecarboxylic acid;

1-cyclopropyl-6,8-difluoro-1,4-dihydro-7-[3-[(methylamino)methyl]-1-pyrrolidinyl]-4-oxo-3-quinolinecarboxylic acid;

1-cyclopropyl-7-[3-(ethylamino)-1-pyrrolidinyl]-6,8-difluoro-1,4-dihydro-4-oxo-3-quinolinecarboxylic acid;

1-cyclopropyl-6,8-difluoro-1,4-dihydro-7-[3-[[(1-methylethyl)amino]methyl]-1-pyrrolidinyl]-4-oxo-3-quinolinecarboxylic acid;

7-(2,5-diazabicyclo[2.2.2]oct-2-yl)-1-cyclopropyl-6,8-difluoro-1,4-dihydro-4-oxo-3-quinolinecarboxylic acid;

7-[3-(exo-amino)-8-azabicyclo[3.2.1]oct-8-yl]-1-cyclopropyl-6,8-difluoro-1,4-dihydro-4-oxo-3-quinolinecarboxylic acid;

7-(1,4-diazabicyclo[3.2.1]oct-4-yl)-1-cyclopropyl-6,8-difluoro-1,4-dihydro-4-oxo-3-quinolinecarboxylic acid;

1-cyclopropyl-6,8-difluoro-1,4-dihydro-7-(5-methyl-2,5-diazabicyclo[2.2.1]hept-2-yl)-4-oxo-3-quinolinecarboxylic acid;

1-cyclopropyl-7-[2,5-diazabicyclo(2.2.1)hept-2-yl]-6,8-difluoro-1,4-dihydro-4-oxo-3-quinolinecarboxylic acid, and the pharmaceutically acceptable acid addition or base salts thereof.

As previously described, the compounds of Formula I are useful as antibacterial agents against both gram-positive and gram-negative bacteria.

An iodotrialkylsilane is one having one to three carbon atoms in the alkyl chain and is, preferably, iodotrimethylsilane. The iodotrialkylsilanes are commercially available or can be prepared, by many known means as, for example, treating a trialkylsilylbromide or chloride with an alkali metal iodide, such as sodium iodide, in an appropriate solvent, e.g., acetone.

The improved process for the preparation of compounds of Formula I proceeds by way of example as follows.

To a solution of a 1-alkyl- or cycloalkyl-6,7,8-trifluoro-1,4-dihydro-4-oxo-3-quinolinecarboxylic acid alkyl ester, in a suitable inert solvent such as ethers, hydrocarbons, acetonitrile, or halocarbons, preferably dichloromethane or chloroform, is added 1.0-3.0 equivalents of an iodotrialkylsilane, under anhydrous conditions.

The reaction mixture is heated at 30°-100° C. and is continued until disappearance of the starting ester is complete, as determined by thin layer chromatography.

The reaction is cooled and concentrated, and the residue taken up in solvents such as acetonitrile, N,N-dimethylformamide, N,N-dimethylacetamide, dimethylsulfoxide, or other aprotic solvents. Alternatively, the desired solvent can be added directly without prior concentration. To this solution is added 1.0-3.0 equivalents of the appropriate amine to be coupled at $C_7$. The mixture is heated at 60°-120° C. until the reaction is complete by thin layer chromatography.

The reaction is cooled. The solids are filtered, washed with inert solvents of choice and dried yielding the desired 7-substituted amino-1-alkyl or cycloalkyl-6,8-difluoro-1,4-dihydro-4-oxo-3-quinolinecarboxylic acid.

The trialkylsilyl ester is removed by the generation of fluoride ion during the course of the displacement reaction.

The starting materials for the present invention are known, or if new, may be prepared from known materials by known means. Thus, ethyl 1-cyclopropyl-6,7,8-trifluoro-1,4-dihydro-4-oxo-3-quinolinecarboxylate is prepared as described in Belgian Pat. No. 899,399 or No. DE3318145. Alternatively, it may be prepared by a series of reactions starting from 2,3,4,5-tetrafluorobenzoic acid. The sodium salt of 2,3,4,5-tetrafluorobenzoic acid is reacted with oxalyl chloride and the product condensed with diethyl malonate in the presence of magnesium turnings to afford after hydrolysis 2,3,4,5-tetrafluorobenzoylacetic acid, ethyl ester. This compound is, in turn, treated with triethylorthoformate and acetic anhydride, followed by cyclopropylamine to afford 2-(2,3,4,5-tetrafluorobenzoyl)-3-cyclopropylamino acrylic acid, ethyl ester, which is then ring closed to give the desired starting material. The corresponding methyl ester is prepared using dimethylmalonate in the sequence described above.

The substituted amines used herein are either known compounds or they may be prepared from known starting materials by standard procedures or by variations thereof. For example, 3-pyrrolidinemethanamines having the structural formula D

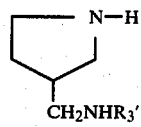

may be readily prepared from the known starting material methyl 5-oxo-1-(phenylmethyl)-3-pyrrolidinecarboxylate, A, [J. Org. Chem., 26, 1519 (1961)] by the following reaction sequence.

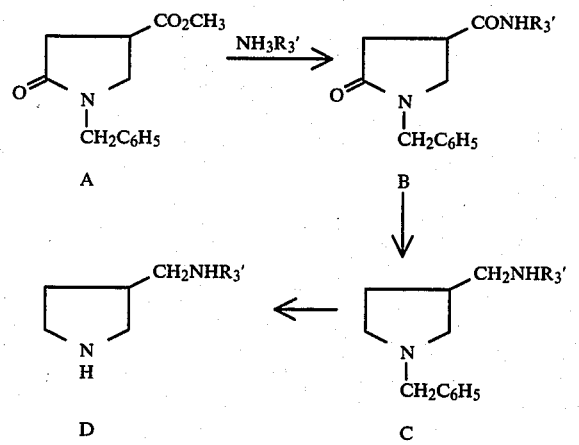

The compound wherein $R_3'$ is hydrogen, namely 3-pyrrolidinemethanamine, has been reported in J. Org. Chem., 26, 4955 (1961).

Thus Compound A may be converted to the corresponding amide B by treatment with $R_3'NH_2$; for example, a saturated solution of ethylamine in an alkanol such as methyl alcohol may be utilized. The diamide B may next be reduced to produce the corresponding diamine C. This reduction may be carried out using lithium aluminum hydride, for example, in a convenient solvent such as tetrahydrofuran. Compound C may next be debenzylated, for example using hydrogen and 20% palladium on carbon catalyst to produce the diamine D. Alternatively, when $R_3=H$ in C, the primary amine function may be protected by acylation with an acyl halide such as acetyl chloride by well known procedures. The primary amine function of C may also be converted to a carbamate ester such as the ethyl ester by treatment with ethyl chloroformate in the presence of a base such as 1,8-diazabicyclo[5.4.0]undec-7-ene in a convenient solvent such as methylene chloride. The benzyl group may next be removed, for example as described above for Compound C, thereby producing Compound D where $R_3$ is $-CO_2Et$. The $-CO_2Et$ group may be removed by standard procedures.

Likewise spiroamino compounds may be readily prepared from the known starting material 3-ethoxycarbonyl-5-oxo-3-pyrrolidineacetic acid ethyl ester [J. Org. Chem., 46, 2757 (1981)] by the following reaction sequence.

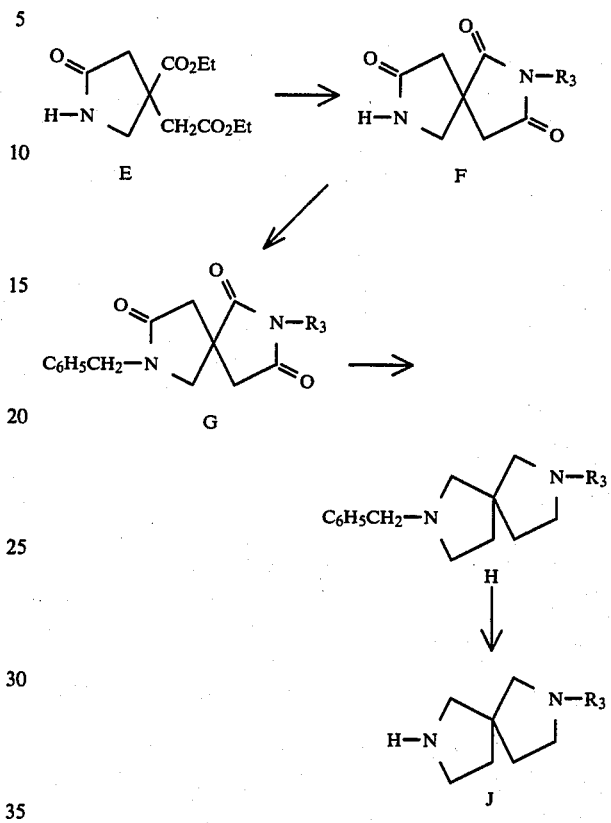

The compound 2,7-diazaspiro[4.4]nonane where $R_3$ is H is described in the above reference. Thus Compound E may be converted to the corresponding amide F by treatment with $R_3NH_2$, for example, methyl amine in water followed by benzylation which may be carried out with sodium hydride and benzyl chloride to give G. Reduction to the diamine H may be accomplished with lithium aluminum hydride. Subsequent debenzylation, for example, with hydrogen and 20% palladium on carbon catalyst produces the diamine J.

The bridged amino compounds are either known compounds or they may be prepared from known starting materials by standard procedures or by variations thereof. For example, exo and endo 3-amino-8-azabicyclo[3.2.1]octanes having the structural formula K and the acetyl derivatives L

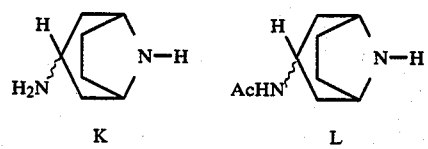

may be readily prepared from the known starting material 8-(phenylmethyl)-8-azabicyclo[3.2.1]octan-3-one oxime, A, [J. Heterocyclic Chem., 19, 485 (1982)] by the following reaction sequence.

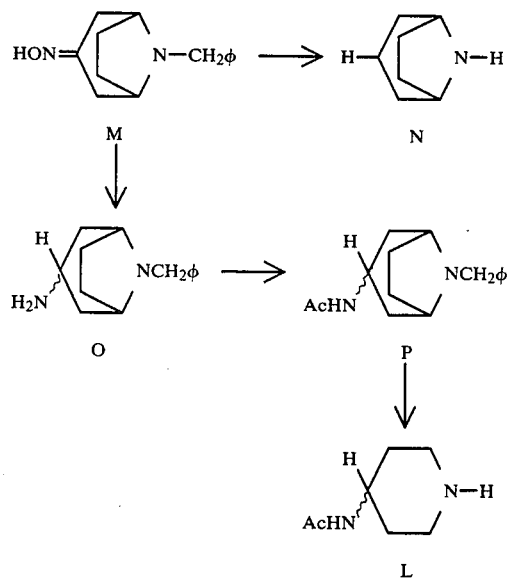

The compounds prepared by the present invention are capable of further forming both pharmaceutically acceptable acid addition and/or base salts. Base salts are formed with metals or amines, such as alkali and alkaline earth metals or organic amines. Examples of metals used as cations are sodium, potassium, magnesium, calcium, and the like. Also included are heavy metal salts such as for example silver, zinc, cobalt, and cerium. Such heavy metal salts are effective in the treatment of burns especially when applied to the affected surface of a burn victim either directly or in combination with a physiologically acceptable carrier such as a water dispersible, hydrophilic carrier. Examples of suitable amines are N,N'dibenzylethylenediamine, chloroprocaine, choline, diethanolamine, ethylenediamine, N-methylglucamine, and procaine.

Pharmaceutically acceptable acid addition salts are formed with organic and inorganic acids.

Examples of suitable acids for salt formation are hydrochloric, sulfuric, phosphoric, acetic, citric, oxalic, malonic, salicylic, malic, gluconic, fumaric, succinic, ascorbic, maleic, methanesulfonic, and the like. The salts are prepared by contacting the free base form with a sufficient amount of the desired acid to produce either a mono or di, etc salt in the conventional manner. The free base forms may be regenerated by treating the salt form with a base. For example, dilute solutions of aqueous base may be utilized. Dilute aqueous sodium hydroxide, potassium carbonate, ammonia, and sodium bicarbonate solutions are suitable for this purpose. The free base forms differ from their respective salt forms somewhat in certain physical properties such as solubility in polar solvents, but the salts are otherwise equivalent to their respective free base forms for purposes of the invention. Use of excess base where R' is hydrogen gives the corresponding basic salt.

The compounds of the invention can exist in unsolvated as well as solvated forms, including hydrated forms. In general, the solvated forms, including hydrated forms and the like are equivalent to the unsolvated forms for purposes of the invention.

Certain compounds of the invention may exist in optically active forms. The pure D isomer, pure L isomer as well as mixtures thereof; including the racemic mixtures, are contemplated by the invention. Additional assymmetric carbon atoms may be present in a substituent such as an alkyl group. All such isomers as well as mixtures thereof are intended to be included in the invention.

The following nonlimiting examples illustrate the inventors' preferred methods for preparing the compounds of the invention.

EXAMPLE 1

1-Cyclopropyl-7-[3-[(ethylamino)methyl]-1-pyrrolidinyl]-6,8-difluoro-1,4-dihydro-4-oxo-3-quinolinecarboxylic acid To a solution of 1.0 g (3.4 mmole) of methyl 1-cyclopropyl-6,7,8-trifluoro-1,4-dihydro-4-oxo-3-quinolinecarboxylate in 25 ml of dichloromethane was added 0.6 ml (0.8 g, 4.2 mmole) of iodotrimethylsilane while stirring at room temperature under a nitrogen atmosphere. The reaction was warmed to reflux and stirred overnight.

The mixture was cooled to room temperature, concentrated, and the residue taken up in 25 ml acetonitrile. To the resulting suspension was added 1.1 g (8.5 mmole) of N-ethyl-3-pyrrolidinemethanamine. The mixture was warmed to reflux for four hours then cooled to room temperature. The formed precipitate was filtered and washed with ether yielding 1.3 g (98%) of the title compound, mp 254°-5°–255.5° C.

Alternatively the ethyl 1-cyclopropyl-6,7,8-trifluoro-1,4-dihydro-4-oxo-3-quinoline carboxylate could be employed as follows.

To a solution of 1.0 g (3.2 mmole) of ethyl 1-cyclopropyl-6,7,8-trifluoro-1,4-dihydro-4-oxo-3-quinoline carboxylate in 25 ml dichloromethane was added 0.6 ml (0.8 g, 4.2 mmole) of iodotrimethylsilane, while stirring at room temperature under a nitrogen atmosphere. The reaction was warmed to reflux and stirred overnight.

An additional 0.23 ml (1.6 mmole) of iodotrimethylsilane was added and the reaction continued at reflux for another 24 hours. The reaction was cooled to room temperature, concentrated, and the residue taken up in 25 ml CH$_3$CN. To the resulting solution was added 1.1 g (8.5 mmole) of N-ethyl-3-pyrrolidinemethaneamine while under nitrogen. The mixture was warmed to reflux for six hours then cooled to room temperature. The solids were filtered and washed with diethyl ether yielding 1.1 g (88%) of the title compound, mp 255°–256° C.

EXAMPLE 2

7-[3-amino-1-pyrrolidinyl]-1-cyclopropyl-6,8-difluoro-1,4-dihydro-4-oxo-3-quinolinecarboxylic acid To a solution of 1.0 g (3.4 mmole) of methyl 1-cyclopropyl-6,7,8-trifluoro-1,4-dihydro-4-oxo-3-quinolinecarboxylate in 25 ml dichloromethane was added 0.6 ml (0.8 g, 4.2 mmole) of iodotrimethylsilane while stirring at room temperature under a nitrogen atmosphere. The mixture was warmed to reflux and stirred overnight. The reaction was cooled to room temperature, concentrated, and the residue taken up in 25 ml acetonitrile. To the resulting suspension was added a solution of 1.6 g (8.5 mmole) of 3-butoxycarbonylaminopyrrolidine bicarbonate in 10 ml acetonitrile while under nitrogen. The reaction was warmed to reflux for four hours, then cooled to room temperature. The formed precipitate was filtered, washed with acetonitrile and ether, yielding 1.26 g (82%) of 7-[3-(butoxycarbonyl)amino-1-pyrrolidinyl]-1-cyclopropyl-6,8-difluoro-1,4-dihydro-4-oxo-3-quinolinecarboxylic acid, mp 228°–230° C.

A solution of 1.26 g (2.80 mmole) of 7-[3-(butoxycarbonyl)amino-1-pyrrolidinyl]-1-cyclopropyl-6,8-difluoro-1,4-dihydro-4-oxoquinoline-3-carboxylic acid in 25 ml of trifluoroacetic acid was stirred at room temperature until gas evolution ceased. The solvent was removed in vacuo and the residue dissolved in 1.0N sodium hydroxide. The solution was diluted to 20 ml with water and acidified to pH 5.5 with 6N hydrochloric acid. The precipitate was removed by filtration, washed with water, ethanol, and ethyl ether. The residue was dried in vacuo to give 0.95 g (97%) of the title compound, mp 290°–292° C.

EXAMPLE 3

1-Cyclopropyl-7-(2,5-diazabicyclo[2.2.1]hept-2-yl)-6,8-difluoro-1,4-dihydro-4-oxo-3-quinolinecarboxylic acid To a solution of 1.0 g (3.4 mmole) of methyl 1-cyclopropyl-6,7,8-trifluoro-1,4-dihydro-4-oxo-3-quinolinecarboxylate in 25 ml dichloromethane was added 0.6 ml (0.8 g, 4.2 mmole) of iodotrimethylsilane while stirring at room temperature under a blanket of nitrogen. The reaction was warmed to reflux and stirred overnight. An additional 0.23 ml (1.6 mmole) of iodotrimethylsilane was added and the solution was refluxed for another two hours, cooled to room temperature, and concentrated. The residue was taken up in 20 ml of acetonitrile. To this solution was added a mixture of 2.2 g (8.5 mmole) of 2,5-diazabicyclo[2.2.1]heptane, dihydrobromide, 2.7 g (17.9 mmole) 1,8-diazobicyclo[5.4.0]undec-7-ene and 20 ml acetonitrile. The reaction was refluxed for 2.5 hours then cooled to room temperature. The formed precipitate was filtered, washed with acetonitrile and ethyl ether, yielding 1.13 g (92%) of the title compound, mp 288°–290° C.

We claim:
1. A process for the preparation of a compound of the formula

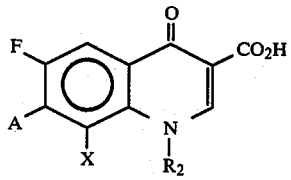

and pharmaceutically acceptable acid addition or base salts thereof, wherein A is, piperazino, N-methylpiperazino or a pyrrolidino group of the formula:

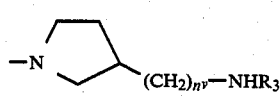

in which $n^v$ is zero or one and $R_3$ is hydrogen, methyl, ethyl, 1- or 2-propyl, a spiroamino group of the formula

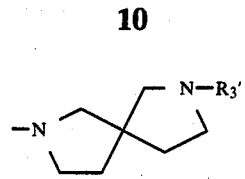

in which $R_3'$ is hydrogen, methyl, ethyl or 1- or 2-propyl; or a bicyclic amino group of the formula

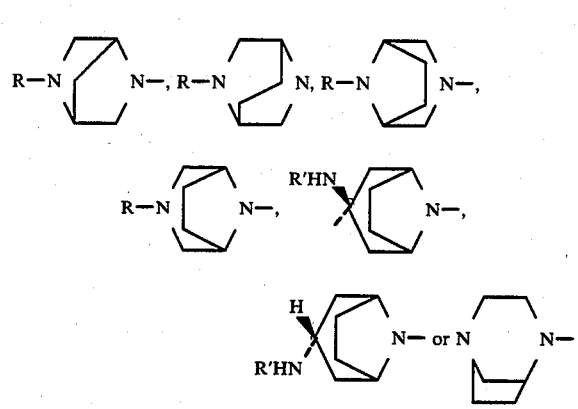

in which R is hydrogen, methyl, ethyl, 1- or 2-propyl, hydroxyethyl, benzyl, or p-aminobenzyl, and R' is hydrogen or acetyl, X is hydrogen or fluorine, and $R_2$ is alkyl of one to three carbon atoms or cycloalkyl of three to six carbon atoms, which comprises:
  (a) reacting 1.0–3.0 equivalent of an iodotrialkylsilane in an inert solvent with a compound of the formula

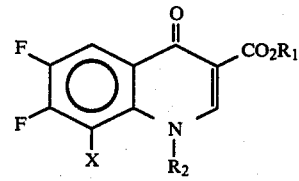

wherein $R_2$ and X are as defined above and $R_1$ is alkyl of one to three carbon atoms, and heating the reaction mixture until the reaction is complete at 30°–100° C. to form a trialkylsilyl ester thereof;
  (b) adding at least one equivalent of the appropriate amine to the trialkylsilyl ester in an aprotic solvent or an aprotic co-solvent and heating the reaction mixture between 60° and 120° C. until the reaction is complete and, if desired, converting by known means the resulting compound of Formula I to a pharmaceutically acceptable acid addition salt thereof.

2. A process according to claim 1, wherein in step (a) an inert solvent is selected from the group consisting of ethers, hydrocarbons, acetonitrile, or halocarbons.

3. A process according to claim 2, wherein dichloromethane, chloroform, or acetonitrile is used.

4. A process according to claim 1, wherein the methyl or ethyl ester of 1-ethyl or 1-cyclopropyl-6,7,8-trifluoro-1,4-dihydro-4-oxo-3-quinolinecarboxylic acid is used as starting material.

5. A process according to claim 1, wherein in step (a) iodotrimethylsilane is used.

6. A process according to claim 1, wherein in step (b) the aprotic solvent is selected from the group consisting of N,N-dimethylformamide, N,N-dimethylacetamide, dimethylsulfoxide, and acetonitrile.

7. A process according to claim 1, wherein A is piperazine, N-methylpiperazine or a pyrrolidine of the formula

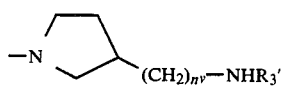

in which $n^v$ is 0 or 1 and $R_3'$ is hydrogen, methyl, ethyl, 1- or 2-propyl.

8. A process according to claim 1, wherein A is of the formula

in which $R_3'$ is hydrogen, methyl, ethyl, 1- or 2-propyl.

9. A process according to claim 1, wherein A is of the formula

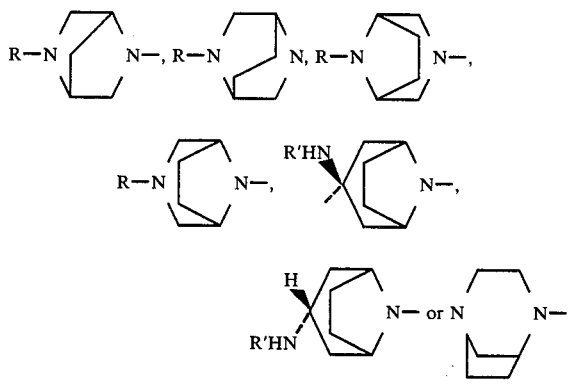

in which R is hydrogen, methyl, ethyl, 1- or 2-propyl, hydroxyethyl, benzyl, or p-aminobenzyl, and R' is hydrogen or acetyl.

10. A process according to claim 1 and for the preparation of 7-[3-(aminomethyl)-1-pyrrolidinyl]-1-cyclopropyl-6,8-difluoro-1,4-dihydro-4-oxo-3-quinolinecarboxylic acid.

11. A process according to claim 1 and for the preparation of 1-cyclopropyl-7-[3-[(ethylamino)-methyl]-1-pyrrolidinyl]-6,8-difluoro-1,4-dihydro-4-oxo-3-quinolinecarboxylic acid.

12. A process according to claim 1 and for the preparation of 7-[3-amino-1-pyrrolidinyl]-1-cyclopropyl-6,8-difluoro-1,4-dihydro-4-oxo-3-quinolinecarboxylic acid.

13. A process according to claim 1 and for the preparation of 1-cyclopropyl-6,8-difluoro-1,4-dihydro-7-[3-[(methylamino)methyl]-1-pyrrolidinyl]-4-oxo-3-quinolinecarboxylic acid.

14. A process according to claim 1 and for the preparation of 1-cyclopropyl-7-[3-(ethylamino)-1-pyrrolidinyl]-6,8-difluoro-1,4-dihydro-4-oxo-3-quinolinecarboxylic acid.

15. A process according to claim 1 and for the preparation of 1-cyclopropyl-6,8-difluoro-1,4-dihydro-7-[3-[[(1-methylethyl)amino]methyl]-1-pyrrolidinyl]-4-oxo-3-quinolinecarboxylic acid.

16. A process according to claim 1 and for the preparation of 7-(2,5-diazabicyclo[2.2.2]oct-2-yl)-1-cyclopropyl-6,8-difluoro-1,4-dihydro-4-oxo-3-quinolinecarboxylic acid.

17. A process according to claim 1 and for the preparation of 7-[3-(exo-amino)-8-azabicyclo[3.2.1]oct-8-yl]-1-cyclopropyl-6,8-difluoro-1,4-dihydro-4-oxo-3-quinolinecarboxylic acid.

18. A process according to claim 1 and for the preparation of 7-(1,4-diazabicyclo[3.2.1]oct-4-yl)-1-cyclopropyl-6,8-difluoro-1,4-dihydro-4-oxo-3-quinolinecarboxylic acid.

19. A process according to claim 1 and for the preparation of 1-cyclopropyl-6,8-difluoro-1,4-dihydro-7-(5-methyl-2,5-diazabicyclo[2.2.1]hept-2-yl)-4-oxo-3-quinolinecarboxylic acid.

20. A process according to claim 1 and for the preparation of 1-cyclopropyl-7-(2,5-diazabicyclo[2.2.1]hept-2-yl)-6,8-difluoro-1,4-dihydro-4-oxo-3-quinolinecarboxylic acid.

21. A process according to claim 1 and for the preparation of 1-ethyl-7-[3-[(ethylamino)methyl]-1-pyrrolidinyl]-6,8-difluoro-1,4-dihydro-4-oxo-3-quinolinecarboxylic acid.

* * * * *